US012773173B2

(12) United States Patent
Rigby et al.

(10) Patent No.: US 12,773,173 B2
(45) Date of Patent: Oct. 27, 2026

(54) SHOULDER MOVEMENT WARNING DEVICE

(71) Applicant: Texas Woman's University, Denton, TX (US)

(72) Inventors: Brandon Rhett Rigby, Denton, TX (US); Hunter Alvis, Denton, TX (US); Mikaela Rood, Madison, WI (US); Lucia Creeden, Burleson, TX (US)

(73) Assignee: TEXAS WOMAN'S UNIVERSITY, Denton, TX (US)

( * ) Notice: Subject to any disclaimer, the term of this patent is extended or adjusted under 35 U.S.C. 154(b) by 252 days.

(21) Appl. No.: 18/638,113

(22) Filed: Apr. 17, 2024

(65) Prior Publication Data

US 2024/0341697 A1 Oct. 17, 2024

Related U.S. Application Data

(60) Provisional application No. 63/496,690, filed on Apr. 17, 2023.

(51) Int. Cl.
*A61B 5/00* (2006.01)
*A61B 5/11* (2006.01)

(52) U.S. Cl.
CPC ............ *A61B 5/746* (2013.01); *A61B 5/1121* (2013.01); *A61B 5/6804* (2013.01); *A61B 5/7455* (2013.01); *A61B 5/6823* (2013.01); *A61B 5/6824* (2013.01); *A61B 2503/20* (2013.01); *A61B 2562/0219* (2013.01)

(58) Field of Classification Search
CPC ..... A61B 5/746; A61B 5/1121; A61B 5/6804; A61B 5/7455; A61B 5/6823; A61B 5/6824; A61B 2503/20; A61B 2562/0219; A61B 5/1116
See application file for complete search history.

(56) References Cited

U.S. PATENT DOCUMENTS 5,791,351 A * 8/1998 Curchod ............ A63B 69/0059 600/595
8,032,199 B2 10/2011 Linti et al.
8,099,258 B2 1/2012 Alten et al.
(Continued)

FOREIGN PATENT DOCUMENTS

CN 104720787 A * 6/2015 ............... A61B 5/16
CN 111603146 A 9/2020
(Continued)

*Primary Examiner* — May A Abouelela
(74) *Attorney, Agent, or Firm* — KOWERT, HOOD, MUNYON, RANKIN & GOETZEL, P.C.; Gareth M. Sampson

(57) ABSTRACT

A shoulder movement warning device is disclosed. The shoulder movement warning device is attached or integrated into a garment worn by a subject or user. The device includes flex sensors and inertial movement unit (IMU) sensors placed at various positions proximate the shoulders and arms of the subject when the garment is worn. The flex sensors and IMU sensors provide detection of angular movement of the shoulders of the subject. When the angular movement exceeds various thresholds for angular movement, the device may provide vibrational feedback to the subject via one or more vibration discs on the garment indicating that shoulder movement is exceeding the thresholds.

20 Claims, 5 Drawing Sheets

(56) References Cited

U.S. PATENT DOCUMENTS

| | | | | |
|---|---|---|---|---|
| 8,475,371 | B2 | 7/2013 | Derchak et al. | |
| 9,345,433 | B1 | 5/2016 | Shinozuka et al. | |
| 9,566,033 | B2 | 2/2017 | Bogdanovich et al. | |
| 9,918,674 | B2 | 3/2018 | Bogdanovich et al. | |
| 9,984,550 | B2 | 5/2018 | Abraham et al. | |
| 10,065,074 | B1 | 9/2018 | Hoang et al. | |
| 10,105,098 | B2 | 10/2018 | Wiebe et al. | |
| 10,166,680 | B2 * | 1/2019 | Hemken | B25J 9/163 |
| 10,251,430 | B2 | 4/2019 | Oleson et al. | |
| 10,456,078 | B2 | 10/2019 | Jayaraman et al. | |
| 10,467,926 | B2 | 11/2019 | Ghaffari et al. | |
| 10,602,929 | B1 * | 3/2020 | McKay | A61B 5/6806 |
| 10,842,415 | B1 * | 11/2020 | Jagannathan | A61B 5/7264 |
| 11,160,971 | B2 * | 11/2021 | Sharma | A61N 1/0484 |
| 11,389,083 | B2 | 7/2022 | Bansbach et al. | |
| 11,497,964 | B1 * | 11/2022 | Hunter | A63B 53/005 |
| 12,471,841 | B1 * | 11/2025 | Allison | A41D 13/1245 |
| 2005/0054941 | A1 * | 3/2005 | Ting | A61B 5/6831 600/534 |
| 2008/0258921 | A1 * | 10/2008 | Woo | G10H 1/40 482/8 |
| 2009/0012408 | A1 | 1/2009 | Nagata et al. | |
| 2010/0026479 | A1 | 2/2010 | Tran | |
| 2011/0060215 | A1 * | 3/2011 | Tupin, Jr. | A61B 5/6833 600/407 |
| 2011/0257928 | A1 * | 10/2011 | Cunningham | A61B 5/1116 324/109 |
| 2012/0139731 | A1 | 6/2012 | Razoumov et al. | |
| 2012/0188083 | A1 | 7/2012 | Miller, II | |
| 2012/0215076 | A1 * | 8/2012 | Yang | A61B 5/6885 600/301 |
| 2012/0238845 | A1 * | 9/2012 | Yang | A61B 5/6805 600/595 |
| 2012/0246795 | A1 | 10/2012 | Scheffler et al. | |
| 2013/0192071 | A1 | 8/2013 | Esposito et al. | |
| 2013/0338472 | A1 | 12/2013 | Barber et al. | |
| 2014/0012161 | A1 * | 1/2014 | Ross, Jr. | A41D 1/002 600/595 |
| 2014/0070957 | A1 | 3/2014 | Longinotti-Buitoni et al. | |
| 2014/0206948 | A1 * | 7/2014 | Romem | A61B 5/6805 600/301 |
| 2015/0045699 | A1 * | 2/2015 | Mokaya | A61B 5/0004 600/595 |
| 2015/0124266 | A1 * | 5/2015 | Davis | A61B 5/1079 356/601 |
| 2015/0335288 | A1 | 11/2015 | Toth et al. | |
| 2015/0366504 | A1 | 12/2015 | Connor | |
| 2016/0038083 | A1 * | 2/2016 | Ding | A61B 5/1135 600/388 |
| 2016/0187166 | A1 | 6/2016 | Ranky et al. | |
| 2016/0202755 | A1 * | 7/2016 | Connor | G06F 3/011 73/865.4 |
| 2016/0279475 | A1 * | 9/2016 | Aragones | G16H 20/30 |
| 2016/0338621 | A1 * | 11/2016 | Kanchan | A61B 5/11 |
| 2016/0338644 | A1 * | 11/2016 | Connor | A61B 5/1126 |
| 2017/0036066 | A1 * | 2/2017 | Chahine | A41D 1/002 |
| 2017/0071548 | A1 * | 3/2017 | Wiebe | G16H 40/67 |
| 2017/0154505 | A1 * | 6/2017 | Kim | G08B 6/00 |
| 2017/0156639 | A1 * | 6/2017 | Gokhale | A61B 5/4561 |
| 2017/0172421 | A1 * | 6/2017 | Dabby | G06F 3/011 |
| 2017/0238849 | A1 * | 8/2017 | Chapman | A61B 5/4576 |
| 2017/0265810 | A1 * | 9/2017 | Van De Vyver | A01K 29/005 |
| 2017/0281074 | A1 * | 10/2017 | D'Lima | A61F 5/3738 |
| 2017/0354353 | A1 * | 12/2017 | Kim | G01L 1/246 |
| 2018/0008196 | A1 * | 1/2018 | Connor | A61B 5/1126 |
| 2018/0116560 | A1 * | 5/2018 | Quinn | A61B 5/02055 |
| 2018/0146922 | A1 * | 5/2018 | Wang | A61B 5/6804 |
| 2018/0160940 | A1 * | 6/2018 | Kim | A61B 5/45 |
| 2018/0192918 | A1 | 7/2018 | Ives | |
| 2018/0242912 | A1 | 8/2018 | Amimori et al. | |
| 2018/0332702 | A1 | 11/2018 | Nakajima et al. | |
| 2019/0029594 | A1 * | 1/2019 | Jiang | A61B 5/6804 |
| 2019/0046114 | A1 * | 2/2019 | Bogdanovich | A61B 5/0205 |
| 2019/0046857 | A1 * | 2/2019 | Sellers, III | A63B 69/0024 |
| 2019/0116892 | A1 | 4/2019 | Scheffler et al. | |
| 2019/0132948 | A1 * | 5/2019 | Longinotti-Buitoni | A61B 5/0022 |
| 2019/0261921 | A1 * | 8/2019 | Otsuka | A61B 5/6805 |
| 2019/0298998 | A1 * | 10/2019 | Coleman | G16H 40/67 |
| 2019/0336038 | A1 * | 11/2019 | Gorgutsa | A61B 5/0816 |
| 2019/0364983 | A1 * | 12/2019 | Nakajima | A41H 3/06 |
| 2020/0000377 | A1 * | 1/2020 | Ly | A61B 5/0022 |
| 2020/0029899 | A1 * | 1/2020 | Bogdanovich | A61B 5/746 |
| 2020/0029900 | A1 * | 1/2020 | Bogdanovich | A61B 5/6804 |
| 2020/0038708 | A1 * | 2/2020 | Cheu | A63B 71/0622 |
| 2020/0107945 | A1 * | 4/2020 | Trousdale | A61B 5/4571 |
| 2020/0129811 | A1 * | 4/2020 | Kruger | A61B 5/0022 |
| 2020/0146594 | A1 * | 5/2020 | Gong | A61B 5/7275 |
| 2020/0337639 | A1 * | 10/2020 | Ruddock | G09B 19/0038 |
| 2020/0352476 | A1 * | 11/2020 | Ladd | G06F 3/14 |
| 2020/0372825 | A1 * | 11/2020 | Ghassemi | A61B 5/1116 |
| 2020/0387227 | A1 * | 12/2020 | Erivantcev | G06F 3/011 |
| 2021/0052199 | A1 * | 2/2021 | Park | A61B 5/1128 |
| 2021/0093230 | A1 * | 4/2021 | Schkommodau | A61B 5/1127 |
| 2021/0100460 | A1 * | 4/2021 | Dagdeviren | G01K 13/20 |
| 2021/0153778 | A1 * | 5/2021 | Gupta | A61B 5/1126 |
| 2021/0315490 | A1 * | 10/2021 | Connor | A61B 5/1126 |
| 2021/0345962 | A1 * | 11/2021 | Fong | A61B 5/1121 |
| 2021/0349529 | A1 * | 11/2021 | Winold | A61B 5/1124 |
| 2021/0380821 | A1 * | 12/2021 | He | A61B 5/112 |
| 2022/0015648 | A1 * | 1/2022 | Zinner | A61B 5/02055 |
| 2022/0039868 | A1 * | 2/2022 | Chaoui | A61B 34/10 |
| 2022/0047181 | A1 * | 2/2022 | Demircan | A61B 5/0024 |
| 2022/0054041 | A1 * | 2/2022 | Menon | G06N 20/00 |
| 2022/0054042 | A1 * | 2/2022 | Kobayashi | A61B 5/0024 |
| 2022/0087607 | A1 * | 3/2022 | Ganesan | B32B 5/26 |
| 2022/0183572 | A1 * | 6/2022 | Korhonen | A61B 5/0022 |
| 2022/0225919 | A1 * | 7/2022 | Cao | A61B 5/361 |
| 2022/0280105 | A1 * | 9/2022 | Dixit | A61B 5/486 |
| 2022/0287651 | A1 * | 9/2022 | Projetti | A61B 5/7264 |
| 2022/0287909 | A1 * | 9/2022 | Sanchez Solana | G16H 20/60 |
| 2022/0296129 | A1 * | 9/2022 | Dodemont | A61B 5/053 |
| 2022/0313119 | A1 * | 10/2022 | Majidi | A61B 5/4848 |
| 2022/0313154 | A1 * | 10/2022 | Meijer | A61B 5/4561 |
| 2022/0330903 | A1 * | 10/2022 | McGovern | A61B 5/7282 |
| 2023/0000423 | A1 * | 1/2023 | Sarkar | A61B 5/4803 |
| 2023/0021704 | A1 * | 1/2023 | Georgeson | A63B 24/0062 |
| 2023/0029417 | A1 * | 1/2023 | Ho | H04B 5/24 |
| 2023/0032821 | A1 * | 2/2023 | Georgeson | A61B 5/458 |
| 2023/0090856 | A1 * | 3/2023 | Tang | A61B 5/332 600/523 |
| 2023/0137521 | A1 * | 5/2023 | Weinstein | A61B 5/02055 600/301 |
| 2023/0233104 | A1 * | 7/2023 | Caviedes | A61B 5/4561 600/595 |
| 2023/0346254 | A1 * | 11/2023 | Bende | A61B 5/688 |
| 2023/0397871 | A1 * | 12/2023 | Crettaz | A61B 5/274 |
| 2023/0404484 | A1 * | 12/2023 | Jennings | A61N 1/36021 |
| 2024/0001196 | A1 * | 1/2024 | Yip | G06N 3/0464 |
| 2024/0032823 | A1 * | 2/2024 | Chahine | A61B 5/6829 |
| 2024/0122499 | A1 * | 4/2024 | Rajkumar | A61B 5/6824 |
| 2024/0130678 | A1 * | 4/2024 | Low | D04B 1/24 |
| 2024/0268756 | A1 * | 8/2024 | Schiller | A61B 5/4528 |
| 2024/0415388 | A1 * | 12/2024 | Kuhnreich | A61B 5/7282 |
| 2025/0144406 | A1 * | 5/2025 | McNutt | A61N 1/0484 |
| 2025/0160714 | A1 * | 5/2025 | Mahnam | A61B 5/6825 |
| 2025/0194985 | A1 * | 6/2025 | Freeman | A61B 5/746 |

FOREIGN PATENT DOCUMENTS

| | | | | |
|---|---|---|---|---|
| WO | WO-2013070171 | A1 * | 5/2013 | A61B 5/7225 |
| WO | WO-2016037068 | A1 * | 3/2016 | A61B 5/389 |
| WO | 2017065272 | A1 | 4/2017 | |
| WO | 2018116424 | A1 | 6/2018 | |
| WO | 2018123034 | A1 | 7/2018 | |
| WO | WO-2022132764 | A1 * | 6/2022 | A61B 5/4566 |
| WO | WO-2022133063 | A1 * | 6/2022 | A61B 5/1122 |

* cited by examiner

SHOULDER MOVEMENT WARNING DEVICE

PRIORITY CLAIM

This application claims priority to U.S. Provisional Application Ser. No. 63/496,690 entitled "SHOULDER MOVEMENT WARNING DEVICE" filed Apr. 17, 2023, which is incorporated herein by reference in its entirety.

BACKGROUND

1. Technical Field

The present disclosure generally relates to a shoulder movement warning device.

2. Description of Related Art

An estimated 4 million U.S. citizens suffer shoulder problems yearly, with shoulder pain affecting 18-26% of adults at any point in time. As one of the most common regional pain syndromes, shoulder pain impacts an individual's daily life, both at home and at the workplace. Moreover, there are a number of economic costs due to increased demands on health care, impaired work performance, substantial sickness absence, and early retirement or job loss.

BRIEF DESCRIPTION OF THE DRAWINGS

Features and advantages of the methods and apparatus of the embodiments described in this disclosure will be more fully appreciated by reference to the following detailed description of presently preferred but nonetheless illustrative embodiments in accordance with the embodiments described in this disclosure when taken in conjunction with the accompanying drawings in which.

Figure 1:
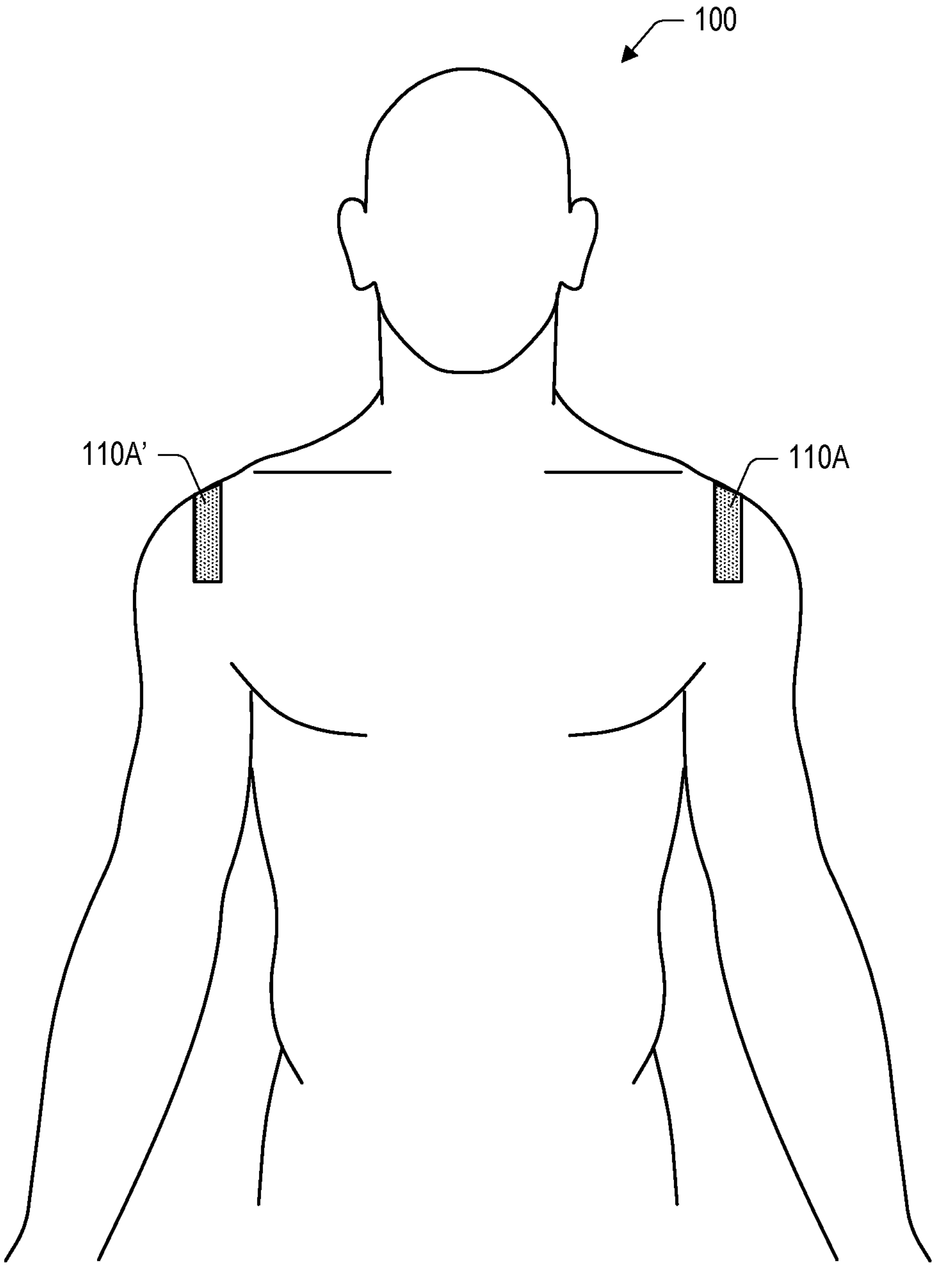
FIG. 1 depicts an anterior view representation of a shoulder movement warning device, according to some embodiments.

This disclosure includes references to "one embodiment," "a particular embodiment," "some embodiments," "various embodiments," or "an embodiment." The appearances of the phrases "in one embodiment," "in a particular embodiment," "in some embodiments," "in various embodiments," or "in an embodiment" do not necessarily refer to the same embodiment. Particular features, structures, or characteristics may be combined in any suitable manner consistent with this disclosure.

Reciting in the appended claims that an element is "configured to" perform one or more tasks is expressly intended not to invoke 35 U.S.C. § 112(f) for that claim element. Accordingly, none of the claims in this application as filed are intended to be interpreted as having means-plus-function elements. Should Applicant wish to invoke Section 112(f) during prosecution, it will recite claim elements using the "means for" [performing a function] construct.

As used herein, the term "based on" is used to describe one or more factors that affect a determination. This term does not foreclose the possibility that additional factors may affect the determination. That is, a determination may be solely based on specified factors or based on the specified factors as well as other, unspecified factors. Consider the phrase "determine A based on B." This phrase specifies that B is a factor that is used to determine A or that affects the determination of A. This phrase does not foreclose that the determination of A may also be based on some other factor, such as C. This phrase is also intended to cover an embodiment in which A is determined based solely on B. As used herein, the phrase "based on" is synonymous with the phrase "based at least in part on."

As used herein, the phrase "in response to" describes one or more factors that trigger an effect. This phrase does not foreclose the possibility that additional factors may affect or otherwise trigger the effect. That is, an effect may be solely in response to those factors, or may be in response to the specified factors as well as other, unspecified factors.

As used herein, the terms "first," "second," etc. are used as labels for nouns that they precede, and do not imply any type of ordering (e.g., spatial, temporal, logical, etc.), unless stated otherwise. As used herein, the term "or" is used as an inclusive or and not as an exclusive or. For example, the phrase "at least one of x, y, or z" means any one of x, y, and z, as well as any combination thereof (e.g., x and y, but not z). In some situations, the context of use of the term "or" may show that it is being used in an exclusive sense, e.g., where "select one of x, y, or z" means that only one of x, y, and z are selected in that example.

In the following description, numerous specific details are set forth to provide a thorough understanding of the disclosed embodiments. One having ordinary skill in the art, however, should recognize that aspects of disclosed embodiments might be practiced without these specific details. In some instances, well-known, structures, computer program instructions, and techniques have not been shown in detail to avoid obscuring the disclosed embodiments.

DETAILED DESCRIPTION

The shoulder joint is a complex joint with multiple bones, muscles, and ligaments working together to support a wide range of motions, especially compared to a simple ball and socket joint. As such, there is a range of causes for shoulder pain and injury. Additionally, shoulder injuries are often caused by excessive, repetitive, overhead motion activities from various sports and during everyday activities, ranging from doing laundry to gardening.

In particular, NASA astronauts face occupational conditions that are prime for shoulder injuries, especially when working inside a space suit in underwater training and extravehicular activity. With this subpopulation in mind, there is a need to develop a shoulder movement warning system that is able to read angular movement at the shoulder and, when an astronaut is in a dangerous position (e.g., when they are in a position that is prone to injury), send tactile feedback via vibration back to the astronaut. Such a device, however, may also have applications in a range of industries, such as the energy industry, where shoulder injuries are a risk to occupational health. For instance, a shoulder movement warning system may be utilized in outpatient rehabilitation, occupational settings, or at-home environments.

The present disclosure contemplates a shoulder movement warning system device that can read angular movement at the shoulder and, when a person (e.g., an astronaut) is in a dangerous position (e.g., when they are in a position prone to injury), send tactile feedback via vibration back to the person. In various embodiments, the device includes various sensors strategically placed on anatomical landmarks in the upper extremity of a user's body in order to track and measure shoulder flexion and shoulder abduction ranges-of-motion, for example, during Extra-Vehicular Activities (EVAs). In some embodiments, the device may provide alerts when the shoulder joint is positioned in dangerous ranges-of-motion via a haptic vibrational drive placed on the posterior scapula. The device may be attached to a wearable garment such as a long sleeve compression shirt. In certain embodiments for astronauts, the garment worn may be similar to the base layer worn under an Extravehicular Mobility Unit (EMU). Such a garment may be able to give a wearer full range of motion and comfortability for long hours (e.g., during astronaut activity). In various embodiments, the garment is fitted to stay in place, flushed against the skin during activity. This may provide more accurate and reliable readings from the sensors, as well as more easily felt tactile feedback from the vibration motors. In some embodiments, pockets are included or added to the garment to secure the components to the garment. The pockets may, in some instances, allow the components to be taken out for charging, replacement, or repairs.

The nature of the device in the disclosed embodiments is such that the warnings provided may not distract the person from his/her current focus (e.g., objectives of his/her training/mission). In summary, the device of the present disclosure is intended to 1) help prevent injury sustained from limitations in the range-of-motion of the glenohumeral joint (e.g., shoulder joint) and 2) help prevent injury by incorporating a sensor that detects how long the person has been in an inverted position (e.g., if an astronaut is in an inverted position for an extended period of time, this can cause injury).

Figure 2A:
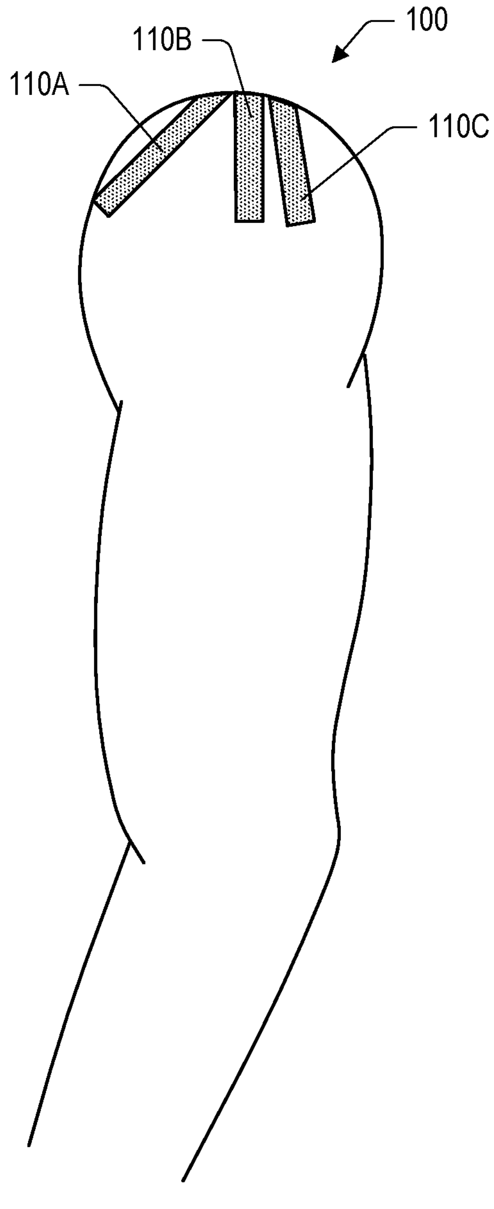
FIG. 2A depicts a side-view representation of a shoulder movement warning device on the left shoulder, according to some embodiments.
Figure 2B:
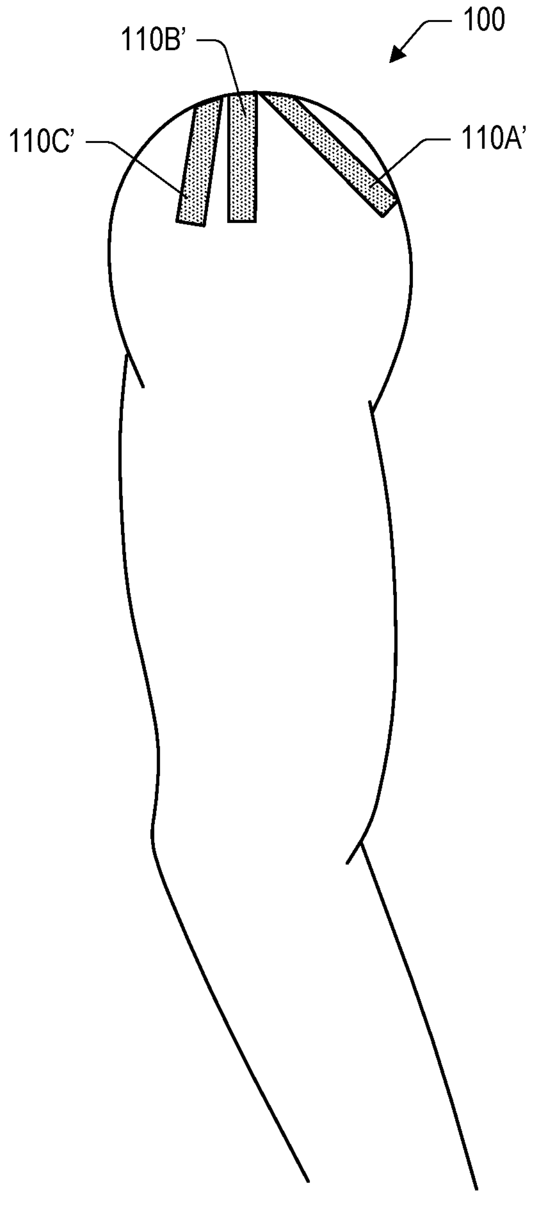
FIG. 2B depicts a side-view representation of a shoulder movement warning device on the right shoulder, according to some embodiments.
Figure 3:
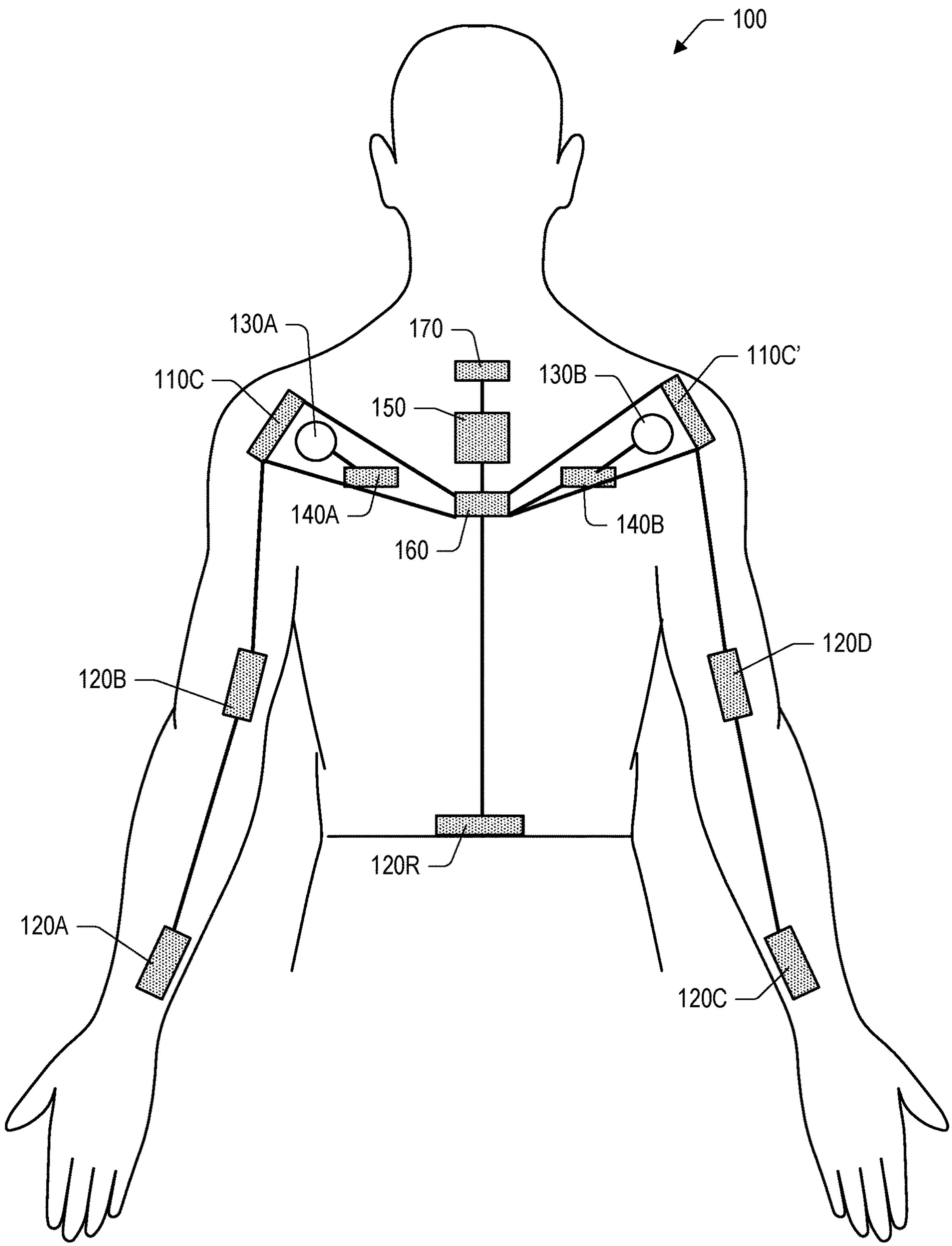
FIG. 3 depicts a posterior representation of a shoulder movement warning device, according to some embodiments.
Figure 4:
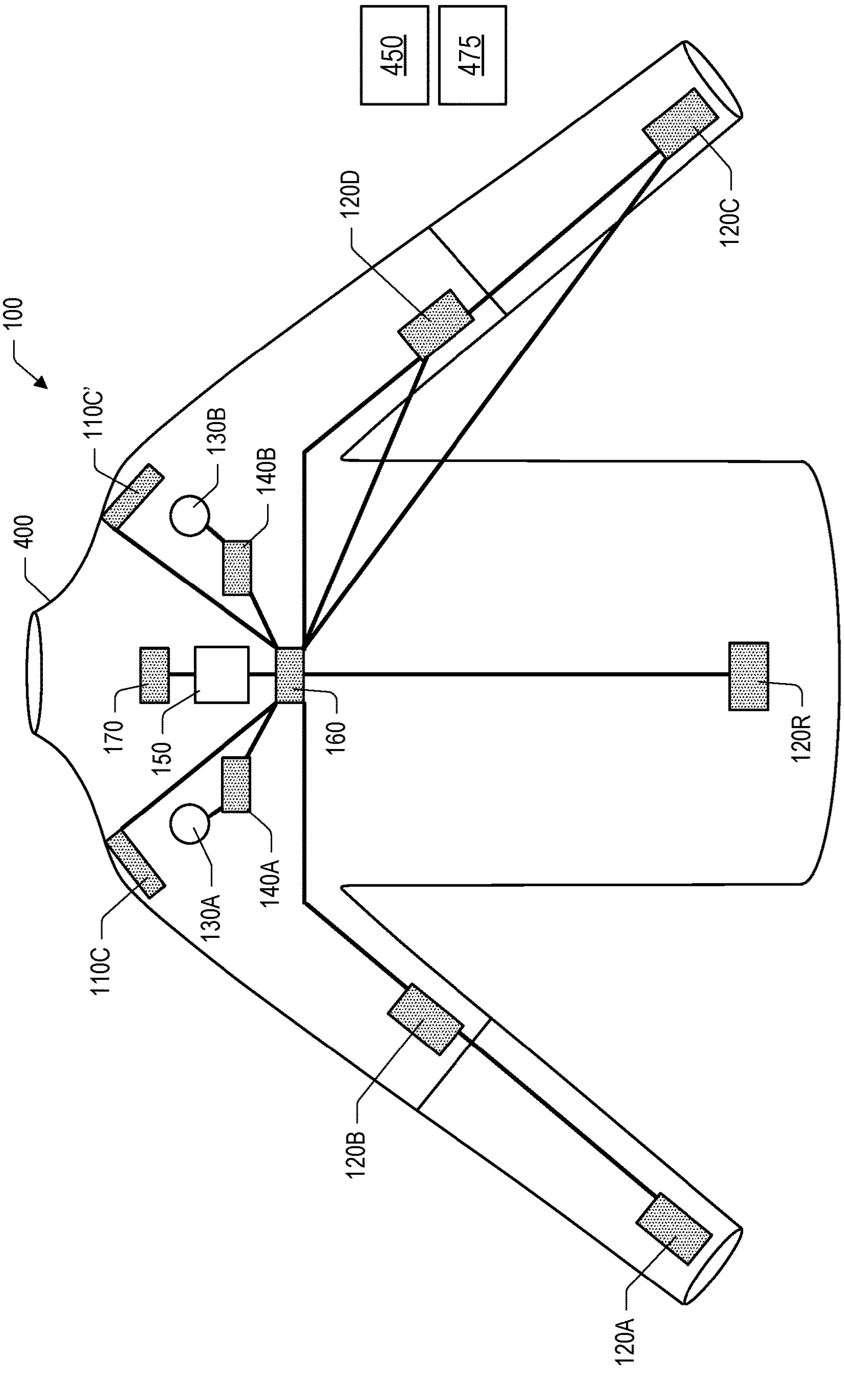
FIG. 4 depicts a posterior representation of a shoulder movement warning device implemented in a garment, according to some embodiments.

FIG. 1 depicts an anterior view representation of a shoulder movement warning device, according to some embodiments. FIG. 2A depicts a side-view representation of a shoulder movement warning device on the left shoulder, according to some embodiments. FIG. 2B depicts a side-view representation of a shoulder movement warning device on the right shoulder, according to some embodiments. FIG. 3 depicts a posterior representation of a shoulder movement warning device, according to some embodiments. It should be noted that the components of shoulder movement warning device 100 are shown with respect to their positioning along an upper body of a subject (e.g., a person) when the shoulder movement warning device 100 is worn as a garment on the upper body by the subject. The garment itself, however, is not shown in FIGS. 1-3 for simplicity in the drawings and to maintain visible views of the components and their positions relative to regions of the upper body of the wearer when shoulder movement warning device 100 is worn as a garment on the upper body. An example of a garment with the components of shoulder movement warning device 100 is shown in the embodiment of FIG. 4, described herein.

In various embodiments, device 100 includes a plurality of flex sensors 110 placed on/around the shoulders of the subject. In certain embodiments, flex sensors 110 are sensors that collect angular feedback through variations in conductivity that occur when the sensor strip (e.g., an electrical sensor strip) is bent (e.g., flexed) as the subject's shoulders move within device 100. One example of a flex sensor is an Adafruit Long Flex Sensor (ADA 182) available from Adafruit Industries (New York, NY). Placement of flex sensors 110 on/around the shoulders of the subject may provide measurement of range-of-motion of the subject's shoulders. For instance, flex sensors 110 may provide measurement of shoulder movements in the sagittal and coronal planes, which are the planes of motion in which shoulder injury most often occurs.

In various contemplated embodiments, flex sensors 110 at or near muscle belly portions of deltoid muscles in one or both the shoulders. For example, in the illustrated embodiments, flex sensors 110 include three flex sensors per shoulder. For the left shoulder, flex sensors 110 include flex sensor 110A placed proximate a muscle belly portion of the anterior deltoid muscle (as shown in FIGS. 1 and 2A), flex sensor 110B placed proximate a muscle belly portion of the middle deltoid muscle (as shown in FIG. 2A) and flex sensor 110C placed between a muscle belly portion of the middle deltoid muscle and a muscle belly portion of the posterior deltoid muscle (as shown in FIGS. 2A and 3). Similarly, for the right shoulder, flex sensors 110 include flex sensor 110A' placed proximate a muscle belly portion of the anterior deltoid muscle (as shown in FIGS. 1 and 2B), flex sensor 110B' placed proximate a muscle belly portion of the middle deltoid muscle (as shown in FIG. 2B) and flex sensor 110C' placed between a muscle belly portion of the middle deltoid muscle and a muscle belly portion of the posterior deltoid muscle (as shown in FIGS. 2B and 3).

Placing flex sensors 110 at the illustrated positions (when a garment supporting device 100 is worn by the subject) provides accuracy in measuring shoulder range-of-motion in the sagittal and coronal planes. Movements measured include flexion and abduction of the shoulders. In various embodiments, warnings may be implemented when flexion and/or abduction movement exceeds predetermined thresholds, as described herein. It should be noted that, in some embodiments, extension and adduction movement of the shoulders may be measured in addition to flexion and abduction movements.

In various embodiments, device 100 includes one or more inertial measurement unit (IMU) sensors 120. One example of an IMU sensor 120 is an Adafruit ISM330DHCX IMU available from Adafruit Industries. Such an IMU sensor includes accelerometer and gyroscope tracking over 6 degrees of freedom. IMU sensors 120 may be placed on the arms of the subject with a reference IMU sensor 120 placed along a vertebrae of the subject. For example, in the illustrated embodiment of FIG. 3, IMU sensors 120 include reference IMU sensor 120R located along the vertebral column of the subject (such as at or near the $4^{th}$ or $5^{th}$ lumbar vertebrae) and two IMU sensors 120A, 120B on the left arm and two IMU sensors 120C, 120D on the right arm. IMU sensors 120A, 120C may be placed on the left and right forearms, respectively, while IMU sensors 120B, 120D may be placed on the left and right upper arms, respectively. In certain embodiments, IMU sensors 120A, 120C are placed on distal thirds of the left and right forearms, lateral and superior to the wrists while IMU sensors 120B, 120D are placed on distal thirds of the left and right upper arms, lateral and superior to the elbows, as shown in FIG. 3.

With these relative placements of IMU sensors 120, movement of IMU sensors 120A-D on the arms of the subject relative to reference IMU sensor 120R may be used to track angular movement of the arms. For instance, movement information from IMU sensors 120A-D may provide angular kinematic data (such as angular velocity and angular acceleration) for the arms. This angular kinematic data provides tracking of shoulder motion (such as internal/external rotation) in addition to tracking of flexion and abduction movement provided by flex sensors 110. Accordingly, combining the angular kinematic data obtained from IMU sensors 120 with the flexion and abduction movement data from flex sensors 110 provides improved tracking of angular movements of the shoulder joints. Additionally, IMU sensors 120 allow for tracking of elbow motion (such as flexion/extension). Tracking of elbow motion may further enhance data collection and data analysis related to treatment of shoulder injuries.

In various embodiments, device 100 includes one or more vibration discs 130. In certain embodiments, device includes one vibration disc 130A placed proximate the posterior of the left shoulder and one vibration disc 130B placed proximate the posterior of the right shoulder. For instance, vibration disc 130A may be placed proximate the left fossa spine (e.g., left posterior scapula) and vibration disc 130B may be placed proximate the right fossa spine (e.g., right posterior scapula). When operated, vibration discs 130 may provide haptic (e.g., vibrational) feedback sensed by the subject. For instance, as described herein, vibrational feedback may be initiated when shoulder movement exceeds a predetermined threshold to warn the subject of dangerous shoulder movement. One example of a vibration disc 130 is an Adafruit vibrating mini motor disc available from Adafruit Industries.

Vibration discs 130 may be driven by haptic motor drivers 140 coupled to the vibration discs. One example of a haptic motor driver is an Adafruit DRV2605L haptic motor controller available from Adafruit Industries. Haptic motor drivers 140 may be placed near their associated vibration discs 130. For instance, haptic motor driver 140A may be placed proximate the left lateral border (e.g., left posterior scapula) and vibration disc 130A while haptic motor driver 140B may be placed proximate the right lateral border (e.g., right posterior scapula) and vibration disc 130B.

In various embodiments, power for the various components of device 100 (e.g., flex sensors 110, IMU sensors 120, and haptic motor drivers 140) may be provided by power source 150. Power source 150 may be, for example, a battery such as a rechargeable battery. In one embodiment, power source 150 may be a lithium ion polymer battery. In certain embodiments, power source 150 is coupled to flex sensors 110, IMU sensors 120, and haptic motor drivers 140 through multiplexor 160. One example of a multiplexor 160 is an Adafruit PCA9548 8-Channel multiplexor available from Adafruit Industries. In various embodiments, power source 150 and multiplexor 160 are positioned along the vertebral column of the subject. For instance, in some contemplated embodiments, power source 150 is placed proximate the $4^{th}$-$6^{th}$ thoracic vertebrae. Multiplexor 160 may then be placed proximate the $8^{th}$-$9^{th}$ thoracic vertebrae.

In certain embodiments, operation of device 100 and data measurement for device 100 is implemented by microcontroller 170. Microcontroller 170 may be coupled to power source 160 and positioned proximate the power source. For instance, microcontroller 170 may be positioned proximate the $2^{nd}$ thoracic vertebrae. One example of microcontroller 170 is an Adafruit STM32F405 Express microcontroller available from Adafruit Industries. In various embodiments, microcontroller 170 includes a port for local memory storage (e.g., via a USB flash device or memory card device). The implementation of the port for local memory storage allows data measurements to be stored locally on microcontroller 170 and easily transferred to an external device (such as external computer) for further processing and/or viewing.

In various embodiments, microcontroller 170 implements various software programmed for operation of device 100. For instance, microcontroller 170 may implement software programmed to implement simultaneous communication, data collection, and data analysis. Simultaneous communication, data collection, and data analysis may simplify data retrieval and analyses and help improve treatment options based on usage of device 100.

As described above, the various components of device 100—including flex sensors 110, IMU sensors 120, vibration discs 130, haptic motor drivers 140, power source 150, multiplexor 160, and microcontroller 170—may be integrated together in a garment that is worn by the subject. FIG. 4 depicts a posterior representation of shoulder movement warning device 100 implemented in a garment, according to some embodiments. In the illustrated embodiment, the components of device 100—flex sensors 110, IMU sensors 120, vibration discs 130, haptic motor drivers 140, power source 150, multiplexor 160, and microcontroller 170—are attached to and/or integrated in garment 400. In certain embodiments, garment 400 is a long sleeve compression shirt that is form fitted to be tightly worn on the upper body of a subject. In some embodiments, the components are placed in pockets in garment 400. The pockets may be, for example, sewn-in pockets of garment 400. Additionally, power source 150, multiplexor 160, and microcontroller 170, as described above, are placed along the superior portion of the vertebral column. This placement may reduce the length of wires needed to reach other components along the shoulders and arms and also improve comfortability for the subject wearing garment 400.

In various embodiments, while garment 400 is worn by a subject, device 100 operates to read movement of the shoulder (or other movement as described herein) and provide tactile feedback (via vibration in vibration discs 130) back to the subject when the movement exceeds one or more predetermined (or programmed) thresholds for movement. For instance, microcontrollers 170 may be programmed to monitor range-of-motion (e.g., flexion, abduction, and/or internal/external rotation movement) of the shoulder joint based on information received from flex sensors 110 and/or IMU sensors 120 and provide output to vibration discs 130 (via haptic motor drivers 140) to vibrate when the shoulders of the subject have movement beyond predetermined thresholds for one or more of the shoulder movements. In some embodiments, the thresholds for providing vibrational feedback may be predetermined angles of flexion or abduction in the shoulders though the internal/external rotation of the shoulders may also be taken into account. The predetermined angle thresholds may be, for example, angles or angular limits that are typically associated with possible injury or damage to the shoulder joints of the subject (e.g., the wearer of garment 400 and device 100). In some embodiments, the vibrational feedback provided by vibration discs 130 may be intended to provide indication to the subject of the risk of injury without distracting the subject from his/her current operation.

In various embodiments, different levels of vibrational (e.g., tactile) feedback are provided at different thresholds (e.g., different angular limits) for shoulder abduction or flexion. For instance, for shoulder abduction, warning zones for possible injury may be defined as (1) 50-75 degrees, (2) 75-100 degrees, and (3) 100-120 degrees while a danger zone (e.g., a zone of high risk of injury) is at angles greater than 120 degrees. For shoulder flexion, the warning zones may be defined as (1) 45-60 degrees, (2) 60-75 degrees, and (3) 75-90 degrees while the danger zone is at angles greater than 90 degrees. In some embodiments, the vibrational feedback may be set to buzz at 60% maximum intensity for warning zone (1), 80% maximum intensity for warning zone (2), and 100% maximum intensity for warning zone (3) while the vibrational feedback is a pulse at 100% maximum intensity for the danger zone. The variation in vibrational feedback may provide sensory input to the subject that is understood to be indicative of the varying levels of warning or danger of injury or other dangers to the shoulder joint.

In certain embodiments, microcontroller 170 provides vibrational feedback independently to the left or right shoulders. For example, vibrational feedback associated with the left shoulder may be provided by activating vibration disc 130A via haptic motor driver 140A and vibrational feedback associated with the right shoulder may be provided by activating vibration disc 130B via haptic motor driver 140A. Accordingly, microcontroller 170 may activate vibration disc 130A (via haptic motor driver 140A) when flex sensors 110 and IMU sensors 120 associated with the left shoulder detect left shoulder movement that has entered a warning or danger zone separately from activating vibration disc 130B (via haptic motor driver 140B) when flex sensors 110 and IMU sensors 120 associated with the right shoulder detect right shoulder movement that has entered a warning or danger zone. Embodiments may also be contemplated where vibrational feedback is provided to both vibration discs 130A and 130B when either shoulder is in the warning zone or danger zone but the intensity is greater in the at risk shoulder. Further embodiments may also include simultaneous same intensity warnings in both shoulders (e.g., when the danger zone is reached).

In some embodiments, microcontroller 170 provides vibrational feedback based on a predetermined time threshold. For instance, microcontroller 170 may be programmed to provide vibrational feedback only after shoulder movement exceeds a predetermined threshold (e.g., angular limit) for a predetermined amount of time. As an example, microcontroller 170 may be programmed to provide vibrational feedback only after shoulder movement is in warning zone (1) for a time period of 5 minutes. In various embodiments, the predetermined amount of time may be different for different warning zones. For instance, the predetermined amount of time for warning zone (2) may be less than the time for warning zone (1) but greater than the time for warning zone (3).

In some embodiments, microcontroller 170 provides vibrational feedback based on a number of repetitions detected in one or more of the warning/danger zones. For instance, vibrational feedback may be provided only after a predetermined number of repetitions in a specific warning zone (or any number or combination of warning zones) is exceeded. As an example, the vibrational feedback may only be provided after a subject has 10 repetitions of shoulder movement that enter warning zone (1) in a given day. Programming of the number of repetitions detected in the warning/danger zones may be useful in utilization of device 100 in rehabilitation programs or other repetitive use programs where incremental shoulder usage is tracked. For instance, such programming of repetitions may be beneficial to allow clients (e.g., users or subjects) to perform a safe number of repetitions in the warning/danger zones before approaching potential shoulder injury. Accordingly, such programming allows a user to perform a safe number of motions in these ranges-of-motion before vibrational feedback begins correcting shoulder motion.

In some embodiments, device 100 may provide tactile feedback (e.g., via vibration discs 130) when the person is in a predefined position for a specified period of time. For example, device 100 may provide tactile feedback when the person is inverted (or within some specified angle of being fully inverted) for a specified period of time. Inversion of the person may be associated with the tilt position measured by the IMU sensors 120. The specified period of time may be, for instance, a period of time at which the person becomes vulnerable to injury when in the inverted position.

In some embodiments, microcontroller 170 is enabled for remote control access by remote control device 450, shown in FIG. 4. Remote control access between microcontroller 170 and remote control device 450 may be provided through infrared communication, Bluetooth communication, or any other wireless communication protocol. For instance, an infrared receiver such as an Adafruit TSOP38238 IR receiver sensor (available from Adafruit Industries) may be coupled to microcontroller 170 to enable remote access via remote control device 450. In some embodiments, remote control device is an Adafruit mini remote control device (available from Adafruit Industries) that provides programmed control through one or more buttons on the device.

In various embodiments, further control of device 100 is provided through user interfaces that interact with microcontroller 170 and/or remote control device 450. For instance, a computational device 475 may be coupled to microcontroller 170 and/or remote control device 450 to provide interaction through a user interface associated with the computational device. Computational device 475 may be, for example, a mobile device (such as a phone or tablet) or a computer (such as a laptop computer) that connects to microcontroller 170 and/or remote control device 450 through a wired or wireless connection and provides a user interface implementing programmability and/or data analysis for device 100.

In some embodiments, microcontroller 170 may be programmable (e.g., via the user interface implemented by computational device 475) to provide modified operating parameters (such as thresholds for warning/danger zones in shoulder abduction or flexion). Modification of operating parameters may, for example, be customized to be user-specific or activity-specific. Accordingly, the warning and danger zones (e.g., shoulder positions that trigger activation of vibration discs 130) of shoulder movement may be customized based on shoulder angle degree and repetitions of shoulder movements in warning/danger zones by modifying the parameters (e.g., thresholds for angular limits or number of repetitions). The modification of parameters thus allows device 100 to be programmed differently based on ideal outcomes (e.g., ideal therapy outcomes) for subjects (e.g., therapy clients).

As one example, device 100 may be programmed for a first client to feel vibrational feedback when the client's shoulder reaches 45 degrees of flexion. Device 100 may be programmed differently for a second client to feel vibrational feedback when the second client's shoulder reaches 90 degrees of flexion. This programming of different angles may be referred to as an "angle degree programming mode". As another example, device 100 may be programmed in a "repetition mode" where vibrational feedback is provided when the client reaches beyond 90 degrees of flexion for a set number of repetitions in a given day (e.g., 10 repetitions).

In various embodiments, device 100 may be programmed to have smaller or larger angular limit values for beginning correctional feedback in a therapeutic activity setting. Setting different angular limit values may be beneficial for clients (e.g., users or subjects) that need to have limits placed on his/her shoulder range-of-motion while allowing the range-of-motion before vibrational feedback to be gradually increased during the rehabilitation process.

In some embodiments, device 100 may be capable of measuring shoulder acceleration and deceleration movements. For instance, IMU sensors 120 may provide data that can be utilized to determine acceleration or deceleration movements in combination with data from flex sensors 110. Having acceleration and deceleration movement data may allow for analysis or detection of potential movements that contribute to injury. For example, a potential movement that can cause injury is deceleration that occurs at the end of a ballistic shoulder/elbow movement (such as shoulder flexion and elbow extension). Such movement can cause numerous injuries to the muscles, bone, and soft tissues at the shoulder, arm, and elbow. Additional embodiments may be contemplated where vibrational feedback is asserted based on tracking of acceleration and deceleration movements. For instance, acceleration or deceleration thresholds may be implemented in device 100 where vibrational feedback is provided when acceleration or deceleration movement tracked by device 100 exceeds or otherwise passes the thresholds.

Example Computer System

Figure 5:
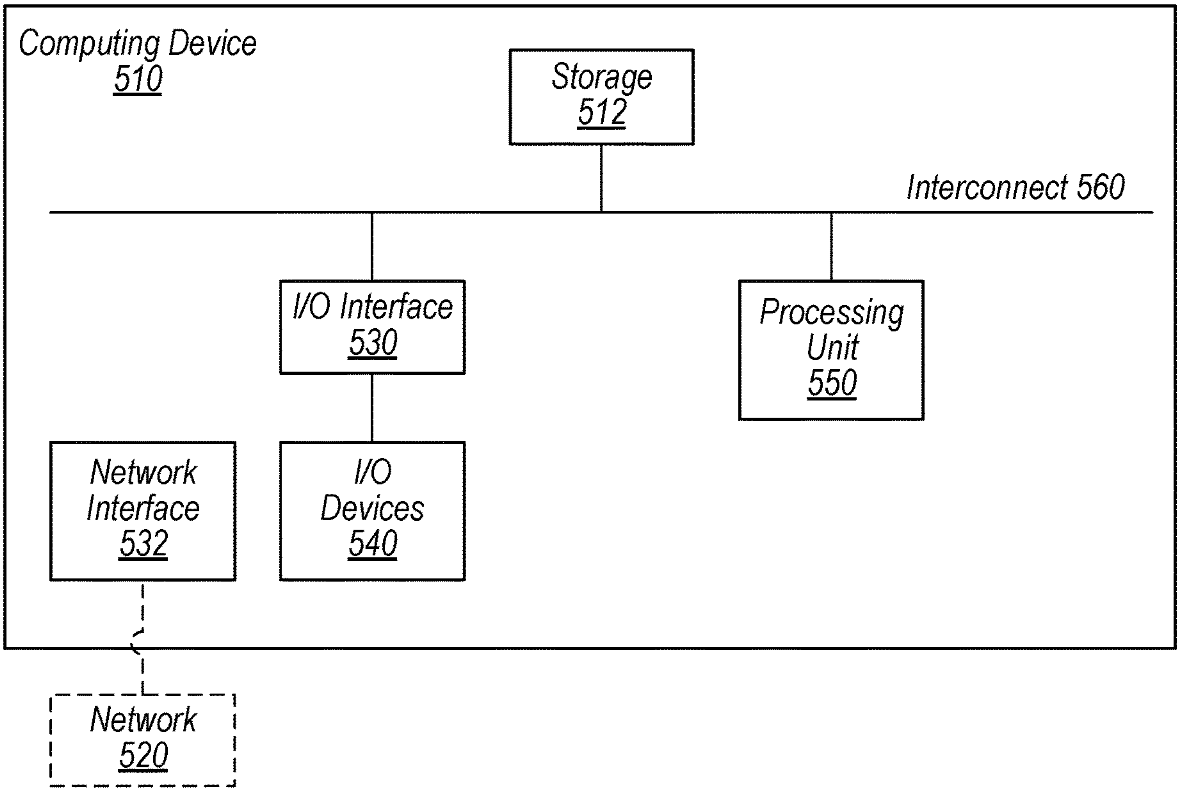
FIG. 5 is a block diagram of one embodiment of a computer system.

Turning now to FIG. 5, a block diagram of one embodiment of computing device (which may also be referred to as a computing system) 510 is depicted. Computing device 510 may be used to implement various portions of this disclosure such as microcontroller 170, remove control device 450, or computational device 475. Computing device 510 may be any suitable type of device, including, but not limited to, a personal computer system, desktop computer, laptop or notebook computer, mainframe computer system, web server, workstation, or network computer. As shown, computing device 510 includes processing unit 550, storage 512, and input/output (I/O) interface 530 coupled via an interconnect 560 (e.g., a system bus). I/O interface 530 may be coupled to one or more I/O devices 540. Computing device 510 further includes network interface 532, which may be coupled to network 520 for communications with, for example, other computing devices.

In various embodiments, processing unit 550 includes one or more processors. In some embodiments, processing unit 550 includes one or more coprocessor units. In some embodiments, multiple instances of processing unit 550 may be coupled to interconnect 560. Processing unit 550 (or each processor within 550) may contain a cache or other form of on-board memory. In some embodiments, processing unit 550 may be implemented as a general-purpose processing unit, and in other embodiments it may be implemented as a special purpose processing unit (e.g., an ASIC). In general, computing device 510 is not limited to any particular type of processing unit or processor subsystem.

As used herein, the term "module" refers to circuitry configured to perform specified operations or to physical non-transitory computer readable media that store information (e.g., program instructions) that instructs other circuitry (e.g., a processor) to perform specified operations. Modules may be implemented in multiple ways, including as a hardwired circuit or as a memory having program instructions stored therein that are executable by one or more processors to perform the operations. A hardware circuit may include, for example, custom very-large-scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, or the like. A module may also be any suitable form of non-transitory computer readable media storing program instructions executable to perform specified operations.

Storage 512 is usable by processing unit 550 (e.g., to store instructions executable by and data used by processing unit 550). Storage 512 may be implemented by any suitable type of physical memory media, including hard disk storage, floppy disk storage, removable disk storage, flash memory, random access memory (RAM-SRAM, EDO RAM, SDRAM, DDR SDRAM, RDRAM, etc.), ROM (PROM, EEPROM, etc.), and so on. Storage 512 may consist solely of volatile memory, in one embodiment. Storage 512 may store program instructions executable by computing device 510 using processing unit 550, including program instructions executable to cause computing device 510 to implement the various techniques disclosed herein.

I/O interface 530 may represent one or more interfaces and may be any of various types of interfaces configured to couple to and communicate with other devices, according to various embodiments. In one embodiment, I/O interface 530 is a bridge chip from a front-side to one or more back-side buses. I/O interface 530 may be coupled to one or more I/O devices 540 via one or more corresponding buses or other interfaces. Examples of I/O devices include storage devices (hard disk, optical drive, removable flash drive, storage array, SAN, or an associated controller), network interface devices, user interface devices or other devices (e.g., graphics, sound, etc.).

Various articles of manufacture that store instructions (and, optionally, data) executable by a computing system to implement techniques disclosed herein are also contemplated. The computing system may execute the instructions using one or more processing elements. The articles of manufacture include non-transitory computer-readable memory media. The contemplated non-transitory computer-readable memory media include portions of a memory subsystem of a computing device as well as storage media or memory media such as magnetic media (e.g., disk) or optical media (e.g., CD, DVD, and related technologies, etc.). The non-transitory computer-readable media may be either volatile or nonvolatile memory.

Although specific embodiments have been described above, these embodiments are not intended to limit the scope of the present disclosure, even where only a single embodiment is described with respect to a particular feature. Examples of features provided in the disclosure are intended to be illustrative rather than restrictive unless stated otherwise. The above description is intended to cover such alternatives, modifications, and equivalents as would be apparent to a person skilled in the art having the benefit of this disclosure.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

What is claimed is:

1. A device, comprising:
- a garment configured to be wearable by a user over left and right shoulders of the user;
- a set of first flex sensors attached to the garment such that the first flex sensors are configured to be positioned proximate muscle belly portions of anterior deltoid muscles of both the left and right shoulders when the garment is worn by the user;
- a set of second flex sensors attached to the garment such that the second flex sensors are configured to be positioned proximate muscle belly portions middle deltoid muscles of both the left and right shoulders when the garment is worn by the user;
- a set of third flex sensors attached to the garment such that the third flex sensors are configured to be positioned between the muscle belly portions of the middle deltoid muscles and muscle belly portions of posterior deltoid muscles of both the left and right shoulders when the garment is worn by the user;
- a set of first inertial movement unit (IMU) sensors attached to the garment such that the first IMU sensors are configured to be positioned on forearm portions of left and right arms of the user;
- a set of second inertial movement unit (IMU) sensors attached to the garment such that the second IMU sensors are configured to be positioned on upper arm portions of the left and right arms of the user;
- a third inertial movement unit (IMU) sensor attached to the garment such that the third IMU sensor is configured to be positioned proximate a vertebral column of the user;
- a first vibration disc attached to the garment such that the first vibration disc is configured to be positioned proximate a posterior portion of the left shoulder when the garment is worn by the user;
- a second vibration disc attached to the garment such that the second vibration disc is configured to be positioned proximate a posterior portion of the right shoulder when the garment is worn by the user; and
- at least one microcontroller coupled to the flex sensors, the IMU sensors, and the vibration discs, wherein the at least one microcontroller is programmed to:
  - assess angular movement of the left and right shoulders of the user based on sensor data from the flex sensors and the IMU sensors; and
  - activate at least one of the first vibration disc and the second vibration disc when the assessed angular movement is beyond a predetermined threshold in a range-of-motion of at least one of the shoulders.

2. The device of claim 1, wherein the predetermined threshold in the range-of-motion of at least one of the shoulders is an angular value for flexion of the at least one of the shoulders.

3. The device of claim 1, wherein the predetermined threshold in the range-of-motion of at least one of the shoulders is an angular value for abduction of the at least one of the shoulders.

4. The device of claim 1, wherein the angular movement of the shoulders includes angular movement in sagittal and coronal planes.

5. The device of claim 1, wherein the flex sensors detect movement through variations in conductivity as the flex sensors are flexed by movement of the user's shoulders.

6. The device of claim 1, wherein the sensor data from the flex sensors includes flexion angular movement data for the shoulders.

7. The device of claim 1, wherein the sensor data from the flex sensors includes abduction angular movement data for the shoulders.

8. The device of claim 1, wherein the IMU sensors include accelerometers and gyroscopes.

9. The device of claim 1, wherein movement of the first IMU sensors and the second IMU sensors relative to the third IMU sensor provides angular kinematic data for movement of the shoulders.

10. The device of claim 1, further comprising a rechargeable power supply coupled to the at least one microcontroller.

11. The device of claim 1, further comprising at least one haptic motor driver coupled to the first vibration disc and at least one haptic motor driver coupled to the second vibration disc.

12. The device of claim 1, wherein the first IMU sensors are positioned on distal thirds of forearms of the left and right arms of the user superior to the wrists.

13. The device of claim 1, wherein the second IMU sensors are positioned on distal thirds of the upper arm portions of the left and right arms of the user superior to the elbows.

14. The device of claim 1, wherein the third IMU sensor is configured to be positioned proximate a lumbar vertebrae of the user.

15. The device of claim 1, wherein the at least one microcontroller is configured to be positioned proximate a thoracic vertebrae of the user.

16. The device of claim 1, wherein the at least one microcontroller is programmed to determine angular velocity data for movement of the shoulders of the user based on the sensor data from the IMU sensors.

17. The device of claim 1, wherein the at least one microcontroller is programmed to activate the vibration discs with varying vibration levels based on the assessed angular movement.

18. A device, comprising:
- a garment configured to be wearable by a user over left and right shoulders of the user;
- a set of first flex sensors attached to the garment such that the first flex sensors are configured to be positioned proximate muscle belly portions of anterior deltoid muscles of both the left and right shoulders when the garment is worn by the user;
- a set of second flex sensors attached to the garment such that the second flex sensors are configured to be positioned proximate muscle belly portions middle deltoid muscles of both the left and right shoulders when the garment is worn by the user;
- a set of third flex sensors attached to the garment such that the third flex sensors are configured to be positioned between the muscle belly portions of the middle deltoid muscles and muscle belly portions of posterior deltoid muscles of both the left and right shoulders when the garment is worn by the user;
- a set of first inertial movement unit (IMU) sensors attached to the garment such that the first IMU sensors are configured to be positioned on forearm portions of left and right arms of the user;
- a set of second inertial movement unit (IMU) sensors attached to the garment such that the second IMU sensors are configured to be positioned on upper arm portions of the left and right arms of the user;

a third inertial movement unit (IMU) sensor attached to the garment such that the third IMU sensor is configured to be positioned proximate a vertebral column of the user;

a first vibration disc attached to the garment such that the first vibration disc is configured to be positioned proximate a posterior portion of the left shoulder when the garment is worn by the user;

a second vibration disc attached to the garment such that the second vibration disc is configured to be positioned proximate a posterior portion of the right shoulder when the garment is worn by the user; and at least one microcontroller coupled to the flex sensors, the IMU sensors, and the vibration discs, wherein the at least one microcontroller is programmed to:

assess angular movement of the left shoulder of the user via the flex sensors positioned proximate the left shoulder and the IMUs positioned along the left arm;

activate the first vibration disc when the assessed angular movement of the left shoulder is beyond a predetermined threshold in a range-of-motion of the left shoulder;

assess angular movement of the right shoulder of the user via the flex sensors positioned proximate the right shoulder and the IMUs positioned along the right arm; and activate the second vibration disc when the assessed angular movement of the right shoulder is beyond a predetermined threshold in a range-of-motion of the right shoulder.

19. The device of claim 18, wherein the at least one microcontroller is programmed to activate the first vibration disc independent of activating the second vibration disc.

20. A method, comprising:

assessing angular movement of a shoulder of a user via a plurality of flex sensors and plurality of inertial movement unit (IMU) sensors positioned in a garment worn by the user, wherein the garment includes:

at least one flex sensor positioned proximate a muscle belly portion of an anterior deltoid muscle of the shoulder;

at least one flex sensor positioned proximate a muscle belly portion of a middle deltoid muscle of the shoulder;

at least one flex sensor positioned between the muscle belly portion of the middle deltoid muscle and a muscle belly portion of a posterior deltoid muscle of the shoulder;

a first IMU sensor positioned on a forearm portion of an arm attached to the shoulder;

a second IMU sensors positioned on an upper arm portion of the arm;

a third IMU sensor positioned proximate a vertebral column of the user; and at least one vibration disc positioned proximate a posterior portion of the shoulder; and activating the at least one vibration disc when the assessed angular movement exceeds a predetermined angular limit for a range-of-motion of the shoulder.

* * * * *